(12) United States Patent
Saito

(10) Patent No.: US 6,566,378 B1
(45) Date of Patent: May 20, 2003

(54) PESTICIDAL COMPOSITIONS AND PESTICIDAL METHODS

(75) Inventor: Shigeru Saito, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 31 days.

(21) Appl. No.: 10/018,766

(22) PCT Filed: Jun. 15, 2000

(86) PCT No.: PCT/JP00/03929

§ 371 (c)(1),
(2), (4) Date: Dec. 21, 2001

(87) PCT Pub. No.: WO01/00027

PCT Pub. Date: Jun. 15, 2000

(30) Foreign Application Priority Data

Jun. 23, 1999 (JP) ............................................ 11-176743

(51) Int. Cl.⁷ ........................ A61K 31/44; A61K 31/535
(52) U.S. Cl. ..................... 514/344; 514/351; 514/229.2
(58) Field of Search ................. 514/344, 351, 514/229.2

(56) References Cited

U.S. PATENT DOCUMENTS

| 5,304,566 A | 4/1994 | Ishimitsu et al. |
| 5,434,181 A | 7/1995 | Kodaka et al. |
| 5,852,012 A | 12/1998 | Maienfisch et al. |

FOREIGN PATENT DOCUMENTS

| EP | 580553 A1 | 1/1994 |
| EP | 649845 A1 | 4/1995 |
| EP | 979606 A1 | 2/2000 |
| FR | 2779032 A1 | 12/1999 |
| JP | 9-151172 A | 6/1997 |
| JP | 11-60413 A | 3/1999 |
| JP | 2000-95612 A | 4/2000 |
| WO | WO 91/04965 A1 | 4/1991 |
| WO | WO 96/11909 | 4/1996 |

*Primary Examiner*—Alton N Pryor
(74) *Attorney, Agent, or Firm*—Birch, Stewart, Kolasch & Birch, LLP

(57) ABSTRACT

A pesticidal composition comprising 3,5-dichloro-1-(3,3-dichloro-2-propenyloxy)-4-[3-(5-trifluoromethylpyridin-2-yloxy)propoxy]benzene and at least one compound selected from the group consisting of (E)-$N^1$-[(6-chloro-3-pyridyl)methyl]-$N^2$-cyano-$N^1$-methylacetamidine, 1-[(tetrahydro-3-furanyl)methyl]-2-nitro-3-methylguanidine and 3-(2-chlorothiazol-5-ylmethyl)-5-methyl-4-nitroiminoperhydro-1,3,5-oxadiazine as active ingredients shows an excellent pesticidal activity.

10 Claims, No Drawings

PESTICIDAL COMPOSITIONS AND PESTICIDAL METHODS

This application is the national phase under 35 U.S.C. §371 of PCT International Application No. PCT/JP00/03929 which has an International filing date of Jun. 15, 2000, which designated the United States of America.

TECHNICAL FIELD

The present invention relates to pesticidal compositions and pesticidal methods.

BACKGROUND ARTS

It is described that (E)-$N^1$-[(6-chloro-3-pyridyl)methyl]-$N^2$-cyano-$N^1$-methylacetamidine, 1-[(tetrahydro-3-furanyl)methyl]-2-nitro-3-methylguanidine and 3-(2-chlorothiazol-5-ylmethyl)-5-methyl-4-nitroiminoperhydro-1,3,5-oxadiazine have pesticidal activity in U.S. Pat. Nos. 5,304,566, 5,532,365 and 5,852,012. Further, WO96/11909 discloses that 3,5-dichloro-1-(3,3-dichloro-2-propenyloxy)-4-[3-(5-trifluoromethylpyridin-2-yloxy)propoxy]benzene has pesticidal activity. However, the pesticidal activities of these compounds are not necessarily sufficient. Therefore, it is desired to develop more excellent pesticides.

DISCLOSURE OF THE INVENTION

The present invention has been found as a result of studying to develop excellent pesticides. According to the present invention, a pesticidal composition comprising 3,5-dichloro-1-(3,3-dichloro-2-propenyloxy)-4-[3-(5-trifluoromethylpyridin-2-yloxy) propoxyl]benzene of the formula (I):

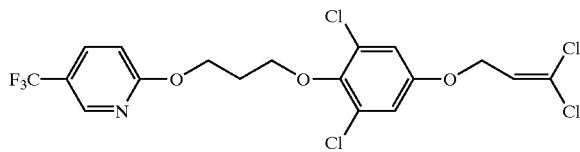

and at least one compound selected from the group consisting of (E)-$N^1$-[(6-chloro-3-pyridyl)methyl]-$N^2$-cyano-$N^1$-methylacetamidine of the formula (A):

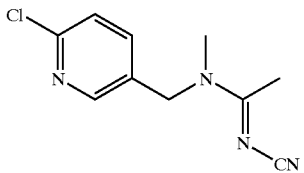

1-[(tetrahydro-3-furanyl)methyl]-2-nitro-3-methylguanidine of the formula (B):

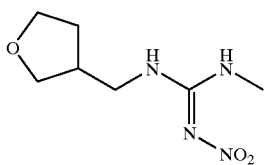

and 3-(2-chlorothiazol-5-ylmethyl)-5-methyl-4-nitroiminoperhydro-1,3,5-oxadiazine of the formula (C):

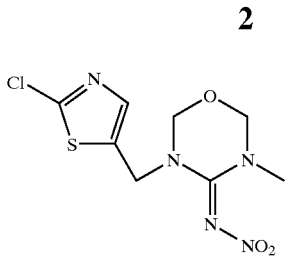

as active ingredients are effective for controlling pests which are insufficiently controlled by each of these compounds solely, and further synergistic joint action gives decrease of an application dosage of each compound.

Namely, the present invention provides a pesticidal composition (hereinafter, referred to as the present composition) comprising 3,5-dichloro-1-(3,3-dichloro-2-propenyloxy)-4-[3-(5-trifluoromethylpyridin-2-yloxy)propoxy]benzene (hereinafter, referred to as Compound (I)), and at least one compound selected from the group consisting of (E)-$N^1$-[(6-chloro-3-pyridyl)methyl]-$N^2$-cyano-$N^1$-methylacetamidine (hereinafter, referred to as Compound A), 1-[(tetrahydro-3-furanyl)methyl]-2-nitro-3-methylguanidine (hereinafter, referred to as Compound B) and 3-(2-chlorothiazol-5-ylmethyl)-5-methyl-4-nitroiminoperhydro-1,3,5-oxadiazine (hereinafter, referred to as Compound C) as active ingredients.

Further, the present invention also provides a pesticidal method comprising utilizing Compound (I) with at least one compound selected from the group consisting of Compound A, Compound B and Compound C together.

Compound (I), Compound A, Compound B and Compound C utilized in the present invention can be obtained according to the descriptions of WO96/11909, U.S. Pat. Nos. 5,304,566, 5,532,365 and 5,852,012 mentioned above.

Examples of the pests against which the present composition gives controlling effect include arthropods such as the following insects and acarina.

Hemipteran pests: Delphacidae (planthoppers) [e.g. *Laodelphax striatellus* (small brown planthopper), *Nilaparvata lugens* (brown planthopper) and *Sogatella furcifera* (whitebacked rice planthopper)], Deltocephalidae and Cicadellidae (leafhoppers) [e.g. *Nephotettix cincticeps* (green rice leafhopper) and *Empoasca onukii* (tea green leafhopper)], Aphididae (aphids) [e.g. *Aphis gossypii* (cotton aphids) and *Myzus persicae* (green peach aphid)], stink bugs, Aleyrodidae (whiteflies) [e.g. *Trialeurodes vaporariorum* (greenhouse whitefly), *Bemisia tabaci* (sweetpotato whitefly) and *Bemisia argentifolli* (silverleaf whitefly)], scales, Tingidae (lace bugs), Psyllidae (suckers) and so on Lepidopteran pests: Pyralidae [e.g. *Chilo suppressalis* (rice stem borer), *Cnaphalocrocis medinalis* (rice leafroller), *Ostrinia nubilalis* (European cornborer), *Parapediasia teterrella* (bluegrass webworm)], Noctuidae [e.g. *Spodoptera litura* (tobacco cutworm), *Spodoptera exigua* (beet armyworm), *Pseudaletia separata* (rice armyworm), *Mamestra brassicae* (cabbage armyworm), Agrotis ipsilon (black cutworm), Trichoplusia spp., Heliothis spp., Heicoverpa spp. and Earias spp.], Pieridae [e.g. Pieris rapae crucivora], Tortricidae [e.g. *Adoxophyes orana fasciata, Grapholita molesta* (oriental fruit moth) and *Cydia pomonella*], Carposinidae [e.g. *Carposina niponensis* (peach fruit moth)], Lyonetiidae [e.g. *Lyonetia clerkella* (peach leafminor)], Gracillariidae [e.g. *Phyllonoryeter ringoniella* (apple leafminor)], Phyllocnistis [e.g. *Phyllocnistis citrella* (citrus leafminor)], Yponameutidae [e.g. *Plutella xylostella*], Gelechiidae [e.g. *Pectinophora gossypiella* (pink bollworm)], Arctiidae (tiger moths), Tineidae and so on; Dipteran pests: Culex spp., Aedes spp., Anopheles spp., Chironomidae (midges), Muscidae (houseflies), Calliphoridae, Sarcophagidae, Anthomyiidae, Cecidomyiidae (gall midges), Agromyzidae (leafminer flies), Tephritidae (fruit flies), Drosophilidae (vinegar flies), Psychodidae (sand flies), Tabanidae, Simuliidae (black flies), Stomoxyidae (stable flies) and so on;

Coleopteran pests: Chrysomelidae (leaf beetles), Scarabaeidae (scarabs), Curculionidae (weevils), Attelabidae, Coccinellidae (ladybirds), Cerambycidae, Tenebrionidae (darkling beetles) and so on; Thysanopteran pests: Thrips spp. [e.g. *Thrips palmi*], *Frankliniela spp.* [e.g. *Frankliniela occidentalis* (western flower thrips)], Scirtothrips spp. [e.g. *Scirtothrps dorsalis* (yellow tea thrips)], Phlaeothripidae and so on; Hymenopteran pests: Tenthredinidae (sawflies), Formicidae (ants), Vespidae (hornets) and so on;

Dictyopteran pests: Blattidae, Blattellidae and so on;

Orthopteran pests: Acrididae (grasshoppers), Gryllotalpidae (mole crickets) and so on;

Siphonapteran pests: *Pulex irritans* (human flea) and so on; Anopluran pests: *Pediculus humanus corporis* (human body louse) and so on;

Isopteran pests; termites

Acarina pests; Tetranychidae (spider mites) [e.g. Tetranychus spp. and Panonychus spp.], Tarsonemidae, Eriophyidae, Acaridae, Ixodidae (ticks) and so on;

The rate of Compound (I) to at least one compound selected from the group consisting of Compound A, Compound B and Compound C in the present composition is usually 1:99 to 90:10, preferably 2:98 to 80:20 by weight ratio.

The present composition can be a mixture of Compound (I) with at least one compound selected from the group consisting of Compound A, Compound B and Compound C, but usually further contain solid carrier, liquid carrier, gaseous carrier, bait, optionally surfactant and the other formulation auxiliaries to be formulated to oil solutions, emulsifiable concentrates, wettable powders, flowables, granules, dusts, aerosols, foggings, smokings, poisonous baits, microcapsules or the like. The total amount of Compound (I), Compound A, Compound B and Compound C in these formulations is usually 0.01 to 95% by weight.

Examples of the solid carrier for formulation include fine powders and granules of clays such as kaolin clay, diatomaceous earth, synthetic hydrated silicon oxide, bentonite, Fubasami clay and terra alba; talc and the like; ceramics; the other inorganic minerals such as sericite, quartz, sulfur, activated carbon, calcium carbonate and hydrated silica; and chemical fertilizers such as ammonium sulfate, ammonium phosphate, ammonium nitrate, urea and ammonium chloride. Examples of the liquid carriers include water; alcohols such as methanol and ethanol; ketones such as acetone and methyl ethyl ketone; aromatic hydrocarbons such as hexane, cyclohexane, kerosene and gas oil; esters such as ethyl acetate and butyl acetate; nitriles such as acetonitrile and isobutyronitrile; ethers such as diusopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cotton seed oil. Examples of the gaseous carrier, namely propellant, include flon gas, butane gas, LPG (liquefied petroleum gas), dimethyl ether and carbon dioxide.

Examples of the surfactant include alkyl sulfate ester salts, alkylsulfonate salts, alkylarylsulfonate salts, alkylaryl ethers and their polyoxyethylenated derivatives, polyethyleneglycol ethers, polyvalent alcohol esters and sugar alcohol derivatives.

Examples of the other formulation auxiliaries such as adhesive agents and dispersants include casein; gelatin; polysaccharides such as starch powder, gum arabic, cellulose derivatives and alginic acid; lignin derivatives; bentonite; sugars; and synthetic water-soluble polymers such as polyvinyl alcohol, polyvinylpyrrolidone and polyacrylic acids. Further, stabilizers including PAP (isopropyl acid phosphate), BHT (2,6-di-tert-butyl-4-methylphenol), BHA (mixture of 2-tert-butyl-4-methoxyphenol and 3-tert-butyl-4- methoxyphenol), vegetable oils, mineral oils, fatty acids and fatty acid esters can be utilized as formulation auxiliaries.

Examples of the poisonous bait materials include diets such as cereal powders, vegetable oils, sugars and crystalline cellulose; antioxidants such as dibutylhydroxytoluene and nordihydroguaiaretic acid; preservatives such as dehydroacetic acid; substances for preventing erroneous eating from children and pets such as red pepper powder; and pest-attractant flavors such as cheese flavor and onion flavor.

The present composition may further contain the other insecticide, acaricide, nematocide, fungicide, herbicide, plant growth regulator, synergist, fertilizer, soil improving agent and so on.

The present composition can also be prepared by mixing each of the active ingredients with the other components mentioned above to be formulated, and then blending them.

The present composition is applied to a pest, place which the pest inhabits, plant to be protected from the pest and so on. In those cases, when the present composition is emulsifiable concentrate, wettable powder, flowable or the like, it is usually diluted with water and then applied. The present composition can be mixed with animal diet and used for controlling pests in cattle house by feed through.

The pesticidal methods of the present invention are usually performed by applying the present composition. However, it is possible to use Compound (I) or its formulation and Compound A, Compound B, Compound C or formulation thereof together, without mixing in advance. In that case, the ratio of Compound (I) to Compound A, Compound B or Compound C is preferably in the same range as the contents of each ingredient in the present composition.

In case of utilizing the present composition for agricultural use, the application rate is usually 0.1 g to 100 g per 1000 m$^2$ at the total amount of the active ingredients. When the present pesticidal composition such as emulsifiable concentrates, wettable powders, flowables and microcapsules is diluted with water and applied, the concentration of the active ingredients is usually 1 ppm to 10000 ppm at the total amount of the active ingredients. Granules, dusts and so on are applied without dilution as they are. Further, in case of utilizing the present composition for household use, emulsifiable concentrates, wettable powders, flowables and microcapsules are diluted with water to make the concentration of the active ingredients to 0.1 ppm to 500 ppm and applied. Oil solutions, aerosols, smokings, poisonous baits and so on are applied as they are.

These application rates and concentrations depend on sorts of formulations, application time, places, methods, sorts of pests, degree of damage and so on, and they can be increased or decreased in spite of the above-mentioned ranges.

EXAMPLES

The present invention will be explained by formulation examples and test examples in detail below. However, the present invention is not limited to these examples.

At first, formulation examples are given, in which part means part by weight.

Formulation Example 1

Emulsifiable Concentrate

One part of Compound (I) and 8 parts of Compound A, Compound B or Compound C are dissolved in 37.5 parts of xylene and 37.5 parts of dimethylformamide. To the solution, 10 parts of polyoxyethylenestyryl phenyl ether and 6 parts of calcium dodecylbenzenesulfonate are added and stirred well to give an emulsifiable concentrate.

Formulation Example 2

Wettable Powders

One part of Compound (I) and 8 parts of Compound A, Compound B or Compound C are added into a mixture of 4 parts of sodium laurylsulfate, 2 parts of calcium ligninsulfonate, 20 parts of fine powders of synthetic hydrated silica and 65 parts of diatomaceous earth, and stirred well to give wettable powders.

Formulation Example 3

Granules

Two parts of Compound (I), 1 part of Compound A, Compound B or Compound C, 5 parts of fine powders of synthetic hydrated silica, 5 parts of sodium dodecylbenzenesulfonate, 30 parts of bentonite and 57 parts of clay are stirred and mixed well. To the mixture, a suitable amount of water is added, further stirred, spherized by granulator and dried through flow to give granules.

Formulation Example 4

Dusts

A half (0.5) part of Compound (I), 4 parts of Compound A, Compound B or Compound C, 1 part of fine powders of synthetic hydrated silica, 1 part of Doriresu B (coagulant manufactured by Sankyo) and 7 parts of clay are mixed well in mortar, and then stirred with juice mixer. To the obtained mixture, 86.5 parts of cut clay are added and stirred well to give dusts.

Formulation Example 5

Flowable

One part of Compound (I), 8 parts of Compound A, Compound B or Compound C and 1.5 parts of sorbitan trioleate are mixed with 26 parts of aqueous solution containing 2 parts of polyvinyl alcohol, and pulverized finely (particle diameter : 3 $\mu$ m or less) by sand grinder. And then, 50 parts of aqueous solution containing 0.05 part of xanthan gum and 0.1 part of aluminum magnesium silicate are added thereto, further 13.5 parts of propylene glycol are added and stirred to give a flowable.

Formulation Example 6

Oil Solution

One-tenth (0.1) part of Compound (I) and 0.8 part of Compound A, Compound B or Compound C are dissolved in 5 parts of xylene and 5 parts of trichloroethane. The solution is mixed with 89.1 parts of deodorized kerosene to give an oil solution.

Formulation Example 7

Oil-based Aerosol

A half (0.5) part of Compound (I) and 4 parts of Compound A, Compound B or Compound C are mixed with 10 parts of trichloroethane and 55.5 parts of deodorized kerosene and dissolved. The solution is charged in an aerosol container, which is followed by attached a valve. Then, 30 parts of propellant (liquefied petroleum gas) is charged under pressure through the valve part to give an oil-based aerosol.

Formulation Example 8

Water-based Aerosol

One-tenth (0.1) part of Compound (I) and 0.8 part of Compound A, Compound B or Compound C are dissolved in 5 parts of xylene, 4.1 parts of deodorized kerosene and 1 part of a surfactant {Atmos 300 (manufactured by Atlas Chemical)}. The solution and 50 parts of purified water are charged into an aerosol container, which is followed by attached a valve. Then, 40 parts of propellant (liquefied petroleum gas) are charged under pressure through the valve part to give a water-based aerosol.

Formulation Example 9

Flowable

One-tenth (0.1) part of Compound (I), 3.2 parts of Compound A, Compound B or Compound C and 1.5 parts of sorbitan trioleate are mixed with 41 parts of aqueous solution containing 2 parts of polyvinyl alcohol, and pulverized finely (particle diameter 3 $\mu$ m or less) by sand grinder. And then, 41 parts of aqueous solution containing 0.05 part of xanthan gum and 0.1 part of aluminum magnesium silicate are added thereto, further 13.2 parts of propylene glycol are added and stirred to give a flowable.

The following test examples show excellent effects of the present composition.

Test Example 1

Test for Controlling Damage by *Helicoverpa Armigera*

Twenty parts of Compound (I) were dissolved in 70 parts of Solvesso 150 (solvent manufactured by Exxon Chemical), and 6 parts of Toximul 3454F (surfactant manufactured by Stepan) and 4 parts of Toximul 3455F (surfactant manufactured by Stepan) were added thereto and mixed well to give an emulsifiable concentrate. An aqueous dilution of the emulsifiable concentrate and an aqueous dilution of a water-soluble formulation of Compound A (commercial name: Mospilan water-soluble formulation produced by Kumiai Chemical Industry) were mixed together to make a designated concentration, to which a spreading agent (New Rinou manufactured by Nihon Nohyaku) was added to make a volume of the spreading agent 1/3000. The prepared application solution was sprayed over potted cabbage (at the fourth to fifth leaf stage) at a volume of 40ml per pot. The treated plants were air dried, and then two fourth-instar larvae of *Helicoverpa armigera* (cotton bollworm) were set free. After 6 days, the damage (%) of the plant was observed. Each controlling ratio (%) was calculated by the following equation based on the damage (%) of non-treated plant.

Controlling ratio (%)=100×(Damage of non-treated plant−Damage of treated plant)/ Damage of non-treated plant The results were given in Table 1.

TABLE 1

| Test compound | Application concentration (ppm) | Controlling ratio (%) |
| --- | --- | --- |
| (I) + Compound A | 2.5 + 100 | 88 |
| (I) + Compound A | 5.0 + 100 | 94 |
| (I) | 2.5 | 25 |
| (I) | 5.0 | 50 |
| Compound A | 100 | 0 |

Test Example 2

Test for Controlling Damage by *Helicoverpa Armigera*

Twenty parts of Compound (I) were dissolved in 70 parts of Solvesso 150 (mentioned above), and 6 parts of Toximul 3454F (mentioned above) and 4 parts of Toximul 3455F (mentioned above) were added thereto and mixed well to give an emulsifiable concentrate. An aqueous dilution of the emulsifiable concentrate and an aqueous dilution of an emulsifiable concentrate, obtained by mixing 10 parts of Compound B or Compound C, 40 parts of xylene, 40 parts of dimethylformamide and 10 parts of Solpol 3005X, were mixed together to make a designated concentration, to which a spreading agent (New Rinou manufactured by Nihon Nohyaku) was added to make a volume of the spreading agent 1/3000. The prepared application solution was sprayed over potted cabbage (at the fourth to fifth leaf stage) at a volume of 40ml per pot. The treated plants were air dried, and then five fourth-instar larvae of Helicoverpa armigera (cotton bollworm) were set free. After 7 days, the damage (%) of the plant was observed. Each controlling ratio (%) was calculated by the following equation based on the damage (%) of non-treated plant.

Controlling ratio (%)=100×(Damage of non-treated plant−Damage of treated plant)/ Damage of non-treated plant The results were given in Table 2.

TABLE 2

| Test compound | Application concentration (ppm) | Controlling ratio (%) |
| --- | --- | --- |
| (I) + Compound B | 2.5 + 200 | 85 |
| (I) | 2.5 | 20 |
| Compound B | 200 | 40 |
| (I) + Compound C | 4 + 100 | 80 |
| (I) | 4 | 40 |
| Compound C | 100 | 0 |

Test Example 3

Test for Controlling Damage by *Aphis Gossypii*

Twenty parts of Compound (I) were dissolved in 70 parts of Solvesso 150 (mentioned above), and 6 parts of Toximul 3454F (mentioned above) and 4 parts of Toximul 3455F (mentioned above) were added thereto and mixed well to give an emulsifiable concentrate. An aqueous dilution of the emulsifiable concentrate and an aqueous dilution of a water-soluble formulation of Compound A (commercial name : Mospilan water-soluble formulation produced by Kumiai Chemical Industry) were mixed together to make a designated concentration, to which a spreading agent (New Rinou manufactured by Nihon Nohyaku) was added to make a volume of the spreading agent 1/5000.

About thirty *Aphis gossypii* (cotton aphid) in various growth stages were set free on potted cucumber (at the first leaf stage), and then the prepared application solution was sprayed over at a volume of 40ml per pot. The treated plants were air dried, covered for preventing escape of the tested aphids and invasion from the outside and set in a greenhouse (25° C.).

Corrected indices were calculated by the following equation based on prerecorded parasitic number of tested aphids on the tested plant before treatment and the parasitic number after two days from the treatment. The corrected index near zero shows high controlling effect.

Corrected index=100×($T_{2DAT}/T_{pre}$)/($C_{2DAT}/C_{pre}$)

$T_{2DAT}$: Number of the tested aphids on the plant after two days from the treatment $T_{pre}$: Number of the tested aphids on the plant before the treatment $C_{2DAT}$: Number of the tested aphids on the plant in non-treated area after two days $C_{pre}$: Number of the tested aphids on the plant in non-treated area at first The results were given in Table 3.

TABLE 3

| Test compound | Application concentration (ppm) | Corrected index |
| --- | --- | --- |
| (I) + Compound A | 0.5 + 0.125 | 3 |
| (I) | 0.5 | 83 |
| Compound A | 0.125 | 29 |

Test Example 4

Test for Controlling Damage by *Aphis Gossypii*

Twenty parts of Compound (I) were dissolved in 70 parts of Solvesso 150 (mentioned above), and 6 parts of Toximul 3454F (mentioned above) and 4 parts of Toximul 3455F (mentioned above) were added thereto and mixed well to give an emulsifiable concentrate. An aqueous dilution of the emulsifiable concentrate and an aqueous dilution of an emulsifiable concentrate, obtained by mixing 10 parts of Compound C, 40 parts of xylene, 40 parts of dimethylformamide and 10 parts of Solpol 3005X, were mixed together to make a designated concentration, to which a spreading agent (New Rinou manufactured by Nihon Nohyaku) was added to make a volume of the spreading agent 1/5000.

About thirty *Aphis gossypii* (cotton aphid) in various growth stages were set free on potted cucumber (at the first leaf stage), and then the prepared application solution was sprayed over at a volume of 40ml per pot. The treated plants were air dried, covered for preventing escape of the tested aphids and invasion from the outside and set in a greenhouse (25° C.).

Corrected indices were calculated by the following equation based on prerecorded parasitic number of tested aphids on the tested plant before treatment and the parasitic number after two days from the treatment. The results were given in Table 4.

TABLE 4

| Test compound | Application concentration (ppm) | Corrected index |
| --- | --- | --- |
| (I) + Compound C | 0.5 + 0.25 | 5 |
| (I) | 0.5 | 83 |
| Compound C | 0.25 | 44 |

What is claimed is:

1. A pesticidal composition which comprises 3,5-dichloro-1-(3, 3-dichloro-2-propenyloxy)-4-[3-(5-trifluoromethylpyridin-2-yloxy)propoxy]benzene and at least one compound selected from the group consisting of (E)-$N^1$-[(6-chloro-3-pyridyl)methyl]-$N^2$-cyano-$N^1$-methylacetamidine, 1-[(tetrahydro-3-furanyl)methyl]-2-nitro-3-methylguanidine and 3-(2-chlorothiazol-5-ylmethyl)-5-methyl-4-nitroiminoperhydro-1,3,5-oxadiazine as active ingredients.

2. The pesticidal composition according to claim 1, which comprises 3,5-dichloro-1-(3,3-dichloro-2-propenyloxy)-4-[3-(5-trifluoromethylpyridin-2-yloxy)propoxy] benzene and (E)-$N^1$-[(6-chloro-3-pyridyl)methyl]-$N^2$-cyano-$N^1$-methylacetamidine as active ingredients.

3. The pesticidal composition according to claim 1, which comprises 3,5-dichloro-1-(3,3-dichloro-2-propenyloxy)-4-[3-(5-trifluoromethylpyridin-2-yloxy)propoxy] benzene and 1-[(tetrahydro-3-furanyl)methyl]-2-nitro-3-methylguanidine as active ingredients.

4. The pesticidal composition according to claim 1, which comprises 3,5-dichloro-1-(3,3-dichloro-2-propenyloxy)-4-[3-(5-trifluoromethylpyridin-2-yloxy)propoxy]benzene and 3-(2-chlorothiazol-5-ylmethyl)-5-methyl-4-nitroiminoperhydro-1,3,5-oxadiazine as active ingredients.

5. The pesticidal composition according to claim 1, wherein the weight ratio of 3,5-dichloro-1-(3,3-dichloro-2-propenyloxy)-4-[3-(5-trifluoromethylpyridin-2-yloxy)propoxy]benzene and at least one compound selected from the group consisting of (E)-$N^1$-[(6-chloro-3-pyridyl)methyl]-$N^2$-cyano-$N^1$-methylacetamidine, 1-[(tetrahydro-3-furanyl)methyl]-2-nitro-3-methylguanidine and 3-(2-chlorothiazol-5-ylmethyl)-5-methyl-4-nitroiminoperhydro-1,3,5-oxadiazine is in the range of from 1:99 to 90:10.

6. A method for controlling pests which comprises applying an effective amount of 3,5-dichloro-1-(3,3-dichloro-2-propenyloxy)-4-[3-(5-trifluoromethylpyridin-2-yloxy)propoxy]benzene and at least one compound selected from the group consisting of (E)-$N^1$-[(6-chloro-3-pyridyl)methyl]-$N^2$-cyano-$N^1$-methylacetamidine, 1-[(tetrahydro-3-furanyl)methyl]-2-nitro-3-methylguanidine and 3-(2-chlorothiazol-5-ylmethyl)-5-methyl-4-nitroiminoperhydro-1,3,5-oxadiazine to the pest, place which the pest inhabits, or plant which is protected from the pest.

7. The method for controlling pests according to claim 6, which comprises applying an effective amount of 3,5-dichloro-1-(3,3-dichloro-2-propenyloxy)-4-[3-(5-trifluoromethylpyridin-2-yloxy)propoxy]benzene and (E)-$N^1$-[(6-chloro-3-pyridyl)methyl]-$N^2$-cyano-$N^1$-methylacetamidine to the pest, place which the pest inhabits, or plant which is protected from the pest.

8. The method for controlling pests according to claim 6, which comprises applying an effective amount of 3,5-dichloro-1-(3,3-dichloro-2-propenyloxy)-4-[3-(5-trifluoromethylpyridin-2-yloxy)propoxy]benzene and 1-[(tetrahydro-3-furanyl)methyl]-2-nitro-3-methyl guanidine to the pest, place which the pest inhabits, or plant which is protected from the pest.

9. The method for controlling pests according to claim 6, which comprises applying an effective amount of 3,5-dichloro-1-(3,3-dichloro-2-propenyloxy)-4-[3-(5-trifluoromethylpyridin-2-yloxy)propoxy]benzene and 3-(2-chlorothiazol-5-ylmethyl)-5-methyl-4-nitroiminoperhydro-1,3,5-oxadiazine to the pest, place which the pest inhabits, or plant which is protected from the pest.

10. The method for controlling pests according to claim 6, wherein the weight ratio of 3,5-dichloro-1-(3,3-dichloro-2-propenyloxy)-4-[3-(5-trifluoromethylpyridin-2-yloxy)propoxy]benzene and at least one compound selected from the group consisting of (E)-$N^1$-[(6-chloro-3-pyridyl)methyl]-$N^2$-cyano-$N^1$-methylacetamidine, 1-[(tetrahydro-3-furanyl)methyl]-2-nitro-3-methylguanidine and 3-(2-chlorothiazol-5-ylmethyl)-5-methyl-4-nitroiminoperhydro-1,3,5-oxadiazine is in the range of from 1:99 to 90:10.

* * * * *